United States Patent [19]

Kimura

[11] Patent Number: 4,528,390

[45] Date of Patent: Jul. 9, 1985

[54] PREPARATION OF POLYMETHYLSILSESQUIOXANE

[75] Inventor: Hiroshi Kimura, Ohta, Japan

[73] Assignee: Toshiba Silicone Co., Ltd., Gunma, Japan

[21] Appl. No.: 623,252

[22] Filed: Jun. 21, 1984

[30] Foreign Application Priority Data

Jul. 5, 1983 [JP] Japan .................................. 58-122217

[51] Int. Cl.³ ........................ C07F 7/08; C08G 77/04; C08G 77/16
[52] U.S. Cl. ........................................ 556/450; 528/21
[58] Field of Search ........................... 556/450; 528/21

[56] References Cited

U.S. PATENT DOCUMENTS 3,637,560 1/1972 Cekada ........................... 556/450 X
4,399,266 8/1983 Matsumura et al. .................. 528/21

*Primary Examiner*—Paul F. Shaver
*Attorney, Agent, or Firm*—Gary L. Loser

[57] ABSTRACT

A process for preparing polymethylsilsesquioxane comprising hydrolyzing and condensing methyltrialkoxysilane or its partially hydrolyzed condensate in an aqueous solution of ammonia or an amine.

4 Claims, No Drawings

PREPARATION OF POLYMETHYLSILSESQUIOXANE

The present patent application claims priority of Japanese patent application Ser. No. 83/122217, filed July 5, 1983.

BACKGROUND OF THE INVENTION

The present invention relates to a process for the preparation of polymethylsilsequioxane. More particularly, the present invention relates to a process for the preparation of polymethylsilsesquioxane powder having an improved flow property.

It is well known in the art that a polymethylsilsesquioxane is obtained by hydrolytic condensation of a trifunctional silane such as methyltrichlorosilane. For example, Belgian Pat. No. 572,412 discloses that methyltrichlorosilane is hydrolyzed by spraying it or adding it dropwise to a large quantity of water to obtain a solid polymethylsilsesquioxane. However, this process has disadvantages in that the rise of temperature owing to the exothermic hydrolysis reaction is great, that a large quantity of hydrogen chloride is generated as a by-product causing corrosion of the apparatus and that the polymethylsilsesquioxane obtained according to the process contains trace amounts of hydrogen chloride as by-product and unhydrolyzed methyltrichlorosilane, so that the chlorine content of the polymethylsilsesquioxane is relatively high. Additionally, the production efficiency of this process is not good because a large quantity of water is needed.

To overcome the disadvantages described above, Japanese Patent Laid-Open No. 72300/1979 proposed that methyltrialkoxysilane and/or its partial hydrolyzate having a chlorine content of from 0.1 to 5.0% by weight is hydrolyzed and condensed in an aqueous solution of an alkaline earth metal hydroxide or an alkali metal carbonate. However, a polymethylsilsesquioxane obtained according to this process contains a relatively large amount of alkaline earth metals or alkali metals. Therefore, when it is used as a filler for a variety of synthetic resins, the resulting compositions tend to be hygroscopic. Furthermore, in this process, the chlorine content of the starting material, i.e. methyltrialkoxysilane, must be controlled to be from 0.1 to 5.0% by weight.

SUMMARY OF THE INVENTION

It is an object of the present invention to provide a process for the preparation of polymethylsilsesquioxane powder which has an improved flow property and a low chlorine content and does not contain alkaline earth metals nor alkali metals.

The present invention relates to a process for the preparation of polymethylsilsesquioxane, characterized in that a methyltrialkoxysilane or its partially hydrolyzed condensate is hydrolyzed and condensed in an aqueous solution of ammonia or an amine.

DESCRIPTION OF THE INVENTION

Methyltrialkoxysilanes or their partially hydrolyzed condensates which are used as starting materials according to the present invention may be obtained by alkoxylation of methyltrichlorosilane with suitable alcohols according to conventional processes. A variety of methyltrialkoxysilanes, such as methyltrimethoxysilane, methyltriethoxysilane, methyltripropoxysilane, and methyltributoxysilane are obtained depending on the particular alcohols used in the alkoxylation. Additionally, partially hydrolyzed condensates of these methyltrialkoxysilanes, which are obtained by hydrolyzing the silanes in the presence of less water than a stoichiometrical quantity, can be used. Among the methyltrialkoxysilanes, methyltrimethoxysilane is preferred from the standpoint of production efficiency.

In the present invention, the chlorine content of a methyltrialkoxysilane or its partially hydrolyzed condensate which is due to hydrogen chloride by-product or unhydrolyzed methylchlorosilane is not critical.

In the present invention, ammonia or amines serve to neutralize chlorine atoms which remain in the alkoxylation product, and act as a catalyst for the hydrolysis and condensation of the methyltrialkoxysilane. Examples of suitable amines include monomethylamine, dimethylamine, monoethylamine, diethylamine and ethylenediamine.

Ammonia is preferred, since it is less toxic and inexpensive, and can be readily removed. Generally, a commercially available aqueous ammonia solution (concentration: 28%) is used.

The amount of ammonia or amine used must be sufficient to neutralize chlorine atoms present in the alkoxysilane or its partially hydrolyzed condensate as described above and to catalyze the hydrolysis and condensation. Furthermore, the amount must be minimized from the standpoint of its removability. If less amounts of ammonia or amine are used, the hydrolysis and condensation of the alkoxysilane will not proceed, and therefore the desired product will not be obtainable.

The amount of an aqueous solution of ammonia or amine used must be sufficient to account for more than twice the stoichiometric amount of water required to hydrolyze the alkoxy groups of the alkoxysilane or its partially hydrolyzed condensate described above and the chlorine atoms of unreacted chlorosilane. The upper limit of the amount of aqueous solution used is not critical. However, if a more aqueous solution is used, it will be disadvantageous to the reaction process and the reaction time will be extended. If a less aqueous solution is used, an alcohol by-product will interfere with the hydrolysis, so that the reaction time will be extended and a powder having an improved flow property will not be obtained.

According to the present invention, the hydrolysis and condensation reaction can be conducted by dropwise addition of a methyltrialkoxysilane to an aqueous solution of ammonia or an amine under stirring. Upon stirring for several hours after the addition, the desired product is obtained. Preferably the hydrolysis-condensation reaction is conducted under heating, since the reaction time can thereby be reduced to obtain the desired product more readily. The heating temperature can be varied depending on the amount of the alkoxysilane or its partially hydrolyzed condensate described above or the amount of aqueous solution of ammonia or amine. Generally the temperature may be the reflux temperature of the reaction mixture. The reaction time is 1 to 2 hours at 70° to 90° C.

When the reaction is conducted under the conditions as described above, a precipitate of polymethylsilsesquioxane separates out as the reaction proceeds. The precipitate is collected, washed with water and dried to give the desired powder product having an improved flow property and good compatibility with synthetic resins.

The polymethylsilsesquioxanes prepared according to the present invention are useful as desiccant for a fire extinguishant powder, as an anti-caking agent for a variety of powder products, as an additive for cosmetics, or as a filler for synthetic resins. For example, when the polymethylsilsesquioxane prepared according to the present invention is added as an extender pigment in place of conventional pigments such as talc or mica powder to a heat-resistant coating material which contains a silicone varnish as the vehicle, the compatibility between the varnish and the extender pigment is excellent so that a coated film having good gloss, improved heat resistance and resistance to cracking or peeling can be formed.

Examples prepared in accordance with the present invention will now be described. In the examples all parts are by weight.

EXAMPLES

EXAMPLE 1

To a 1 liter four-necked flask fitted with a thermometer, a reflux condenser and a stirrer were charged 500 parts of water and 50 parts of a 28% aqueous solution of ammonia. 200 parts of methyltrimethoxysilane containing 5 ppm (in terms of chlorine atom) methyltrichlorosilane was added dropwise to the flask over 40 minutes while stirring. The reaction temperature was 10° C. at the beginning, and reached 30° C. at the end of the addition. The mixture was refluxed at 84° C. by a mantle heater for about an hour. After cooling the mixture, a precipitated product was collected, washed with water and dried to obtain polymethylsilsesquioxane powder having improved flow property. The product contained not more than 0.1 ppm of chlorine atom.

EXAMPLES 2 TO 5

In each example, the same procedure as described in Example 1 was repeated except that methyltrimethoxysilane and aqueous ammonia as shown in Table 1 were used. The properties, chlorine contents and rates of moisture absorption of the resulting products are also shown in Table 1. Additionally, comparative experiments were conducted according to the procedure as described in Example 1 except that an aqueous solution of calcium hydroxide was used in Comparative Example 1 instead of an aqueous ammonia, an aqueous solution of sodium hydroxide was used in Comparative Example 2, and methyltrichlorosilane was used in Comparative Example 3 instead of methyltrimethoxysilane.

TABLE 1

|  | Example 2 | Example 3 | Example 4 | Example 5 | Comp. Ex. 1 | Comp. Ex. 2 | Comp. Ex. 3 |
| --- | --- | --- | --- | --- | --- | --- | --- |
| Methyltrimethoxy silane (parts) | 200 | 200 | 200 | 200 | 150 | 200 | $CH_3SiCl_3$ 200 |
| Chlorine content (%) | (1%) | (100 ppm) | (1 ppm) | (0.1%) | (0.1%) | (10 ppm) |  |
| Aqueous ammonia (parts) | 700 | 700 | 500 | 750 | 1% $CaOH_2$ aqueous solution 750 | 1% NaOH aqueous solution 200 | 700 |
| (concentration) | (5%) | (2.5%) | (5%) | (1%) |  |  | (5%) |
| Product Property | powder having an improved flow property | powder having an improved flow property | powder having an improved flow property | powder having an improved flow property | gelled upon heating under reflux | gelled | gelled |
| Chlorine content | up to 5 ppm | up to 1 ppm | up to 0.1 ppm | up to 1 ppm | — | — | — |
| Rate of moisture absorption | up to 1% | up to 1% | up to 1% | up to 1% | — | — | — |

EXAMPLE 6

9 parts of water was added to 178 parts of methyltriethoxysilane containing 1% by weight of chlorine atoms. The mixture was heated at 80° C. for 2 hours to obtain its partially hydrolyzed condensate. This condensate was added dropwise to 500 parts of a 3% aqueous solution of ethylenediamine, and hydrolyzed and condensed under the conditions as described in Example 1 to obtain a polymethylsilsesquioxane powder.

REFERENTIAL EXAMPLE 125 g of the polymethylsilsesquixoane powder prepared according to each of Examples 1 to 6, 125 g of Ceramic Black 4001 (a product of Nemoto Chemie, Ltd.) and 500 g or silicone varnish TSR145 (a product of Toshiba Silicone Co., Ltd., resin content: 60%) were milled by a ball mill to prepare a heat-resistant coating material.

Additionally, comparative coating materials A and B were prepared according to the same procedure as described above except that no extender filler such as polymethylsilsesquioxane was used in comparative coating material A and that 100 g of talc and 25 g of mica were used as extender fillers instead of polymethylsilsesquioxane in comparative coating material B.

Each coating material was applied on a rolled steel plate (150 mm × 50 mm × 0.3 mm) to form a coated film having a thickness of 30 to 40 μm. The coated film was cured by heating at 200° C. for 60 minutes. The specular reflectivity at an angle of 60° of the resulting coated film was measured to examine the gloss. Furthermore, after the sample had been placed in an atmosphere of 300° C. for 200 hours, the coated film was examined for cracking and peeling. The results are shown in Table 2.

TABLE 2

|  | Coating material using the product of Example 1 | Coating material using the product of Example 2 | Coating material using the product of Example 3 | Coating material using the product of Example 4 | Coating material using the product of Example 5 | Coating material using the product of Example 6 | Comparative coating material A | Comparative coating material B |
| --- | --- | --- | --- | --- | --- | --- | --- | --- |
| Thickness of coated film (μm) | 35~40 | 32~38 | 31~35 | 30~35 | 35~40 | 33~39 | 32~34 | 30~35 |

TABLE 2-continued

| | Coating material using the product of Example 1 | Coating material using the product of Example 2 | Coating material using the product of Example 3 | Coating material using the product of Example 4 | Coating material using the product of Example 5 | Coating material using the product of Example 6 | Comparative coating material A | Comparative coating material B |
| --- | --- | --- | --- | --- | --- | --- | --- | --- |
| Gloss, specular reflectivity at an angle of 60° | 85 | 84 | 84 | 86 | 86 | 84 | 92 | 40 |
| Heat resistance 300° C. × 200 hours | no cracking no peeling | no cracking no peeling | no cracking no peeling | no cracking no peeling | no cracking no peeling | no cracking no peeling | peeling | no cracking no peeling |

It is apparent from Table 2 that the heat-resistant coating materials using polymethylsilsesquioxane prepared in Examples 1 to 6 can form coated films having high heat resistance and good gloss.

As described above, the process of the invention can afford a polymethylsilsesquioxane which does not contain alkaline earth metals nor alkali metals and has less chlorine content and an improved flow property.

I claim:

1. A process for preparing polymethylsilsesquioxane comprising hydrolyzing and condensing methyltrialkoxysilane or its partially hydrolyzed condensate in an aqueous solution of ammonia or an amine.

2. A process as set forth in claim 1 wherein the methyltrialkoxysilane is methyltrimethoxysilane.

3. A process as set forth in claim 1 wherein the aqueous solution of ammonia or an amine is an aqueous ammonia solution.

4. A process as set forth in claim 1 further comprising heating the solution so as to accelerate condensation.

* * * * *